(12) United States Patent
Duan et al.

(10) Patent No.: US 6,406,669 B1
(45) Date of Patent: Jun. 18, 2002

(54) POLYANILINE-BASED OPTICAL AMMONIA DETECTOR

(75) Inventors: Yixiang Duan; Zhe Jin; Yongxuan Su, all of Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/760,121

(22) Filed: Jan. 12, 2001

(51) Int. Cl.$^7$ ............................................... G01N 21/77
(52) U.S. Cl. ....................... 422/82.09; 422/91; 436/113
(58) Field of Search ............................... 422/82.09, 88, 422/91; 436/113, 164, 167, 171

(56) References Cited

U.S. PATENT DOCUMENTS

| | | | |
|---|---|---|---|
| 5,164,465 A | * 11/1992 | Epstein et al. | 525/540 |
| 5,198,153 A | * 3/1993 | Angelopoulos et al. | 252/500 |
| 5,208,301 A | * 5/1993 | Epstein et al. | 525/540 |
| 5,252,292 A | 10/1993 | Hirata et al. | 422/98 |
| 6,051,437 A | 4/2000 | Luo et al. | 436/172 |
| 6,117,686 A | 9/2000 | Tanaka et al. | 436/167 |

OTHER PUBLICATIONS

Stejskal, J. et al "Polyaniline dispersions. 2. UV–Vis absorption spectra" Synt. Met. (1993), vol. 61, No. 3, pp. 225–231, Abstract only.*

Yuan, J. et al "Fiber optic chemical sensors using a modified conducting polymer cladding" Proc. SPIE Int. Soc. Opt. Eng. (2001), vol. 4205 (Advanced Environmental and Chemical Sensing Technology), pp. 170–179, Abstract only.*

N.C. Foulds and C.R. Lowe, "Immobilization Of Glucose–Oxidase In Ferrocene–Modified Pyrrole Polymers", Analytical Chemistry 60, 2473–2478 (1988).

O.A. Sadik and G.G. Wallace, "Pulsed Amperometric Detection Of Proteins Using Antibody Containing Conducting Polymers", Analytica Chimica Acta 279, 209–212 (1993).

S. Demarcos and O.S. Wolfbeis, "Optical Sensing Of pH Based On Polypyrrole Films", Analytica Chimica Acta 334, 149–153 (1996).

M. Bile et al., "The Effect Of Initial Conductivity And Doping Anions On Gas Sensitivity Of Conducting Polypyrrole films to $NH_3$", Sensors and Actuators B37, 119–122 (1996).

S.A. Krutovertsev et al., "Polymer Film–Based Sensors For Ammonia Detection", Sensors And Actuators B7, 492–494 (1992).

A.L. Kukla et al., "Ammonia Sensors Based On Sensitive Polyaniline Films", Sensors and Actuators B37, 135–140 (1996).

N.E. Agbor et al., "Polyaniline Thin Films For Gas Sensing", Sensors and Actuators B28, 173–179 (1995).

F. Musio et al., "High–Frequency a.c. Investigation Of Conducting Polymer Gas Sensors", Sensors and Actuators B23, 223–226 (1995).

(List continued on next page.)

*Primary Examiner*—Jeffrey Snay
(74) *Attorney, Agent, or Firm*—Samuel M. Freund

(57) ABSTRACT

Electronic absorption spectroscopy of a polyaniline film deposited on a polyethylene surface by chemical oxidation of aniline monomer at room temperature was used to quantitatively detect ammonia gas. The present optical ammonia gas detector was found to have a response time of less than 15 s, a regeneration time of less than 2 min. at room temperature, and a detection limit of 1 ppm (v/v) for ammonia, with a linear dynamic range from 180 ppm to 18,000 ppm.

6 Claims, 6 Drawing Sheets

OTHER PUBLICATIONS

M.E.H. Amrani et al., "Multi–Frequency Measurements Of Organic Conducting Polymers For Sensing Of Gases And Vapors", Sensors And Actuators B33, 137–141 (1996).

M.E.H. Amrani et al., "Frequency Counting Interrogation Techniques Applied To Gas Sensor Arrays", Sensors and Actuators B57, 75–82, (1999).

N.E. Agbor et al., "An Optical Gas Sensor Based On Polyaniline Langmuir–Blodgett Films", Sensors and Actuators B41, 137–141 (1997).

E. Pringsheim et al., "Optical Sensing Of pH Using Thin Films Of Substituted Polyanilines", Analytica Chimica Acta 357, 247–252 (1997).

* cited by examiner

POLYANILINE-BASED OPTICAL AMMONIA DETECTOR

STATEMENT REGARDING FEDERAL RIGHTS

This invention was made with government support under Contract No. W-7405-ENG-36 awarded by the U.S. Department of Energy to The Regents of The University of California. The government has certain rights in the invention.

FIELD OF THE INVENTION

The present invention relates generally to apparatus for detecting ammonia in fluids and, more particularly, to the use of electronic absorption spectroscopy for determining the quantity of ammonia that has reacted with a conducting polymer film in contact therewith.

BACKGROUND OF THE INVENTION

Conducting polymers which can be prepared by a simple oxidative polymerization method have found use as chemical and biological sensors. They exhibit reversible pH-induced spectroscopic and gas-induced conductivity changes. Such materials also provide a suitable structure for immobilization of ligands, enzymes, and antibodies. See, e.g., "Immobilization Of Glucose-Oxidase In Ferrocene-Modified Pyrrole Polymers" by N. C. Foulds and C. R. Lowe, Analytical Chemistry 60, 2473–2478 (1988); "Pulsed Amperometric Detection Of Proteins Using Antibody Containing Conducting Polymers" by O. A. Sadik and G. G. Wallace, Analytica Chimica Acta 279, 209–212 (1993); and "Optical Sensing Of pH Based On Polypyrrole Films" by S. Demarcos and O. S. Wolfbeis, Analytica Chimica Acta 334, 149–153 (1996).

Conducting polymer gas sensors commonly rely on conductivity changes that occur when they are exposed to certain gases. For example, the dc conductivity of a polypyrrole film decreases with increasing ammonia gas concentration, and an ammonia gas sensor based on this property has been developed (See, e.g., "The Effect Of Initial Conductivity And Doping Anions On Gas Sensitivity Of Conducting Polypyrrole films to $NH_3$" by M. Bile et al., Sensors and Actuators B37, 119–122 (1996)). At room temperature, the response time of such a sensor was found to be a few tens of minutes. By increasing the temperature from 20 to 100° C., the response time was shortened by a factor of five. After treatment with $NO_2$, the response and sensitivity of the sensor deteriorated. The major problems of this polypyrrole ammonia gas sensor are slow response time, low sensitivity, irreversible response, and a controlled high temperature (100° C.) requirement.

The dc conductivity of polyaniline films also changes when the films are exposed to ammonia gas. For example, a polyaniline film containing nickel prepared by electrochemical oxidation can be used to detect ammonia gas in the range between 1 and 10,000 PPM at room temperature (See, e.g., "Polymer Film-Based Sensors For Ammonia Detection" by S. A. Krutovertsev et al., Sensors And Actuators B7, 492–494 (1992)). The response time was reported to be approximately two minutes which is much faster than that for a polypyrrole ammonia sensor; however, the regeneration of the polyaniline sensor was slow (See, e.g., "Ammonia Sensors Based On Sensitive Polyaniline Films" by A. L. Kukla et al., Sensors and Actuators B37, 135–140 (1996)). By heating the sensor layer to between 104 and 107° C., it was possible to completely regenerate the sensor within a short period of time. Polyaniline films are also sensitive to $H_2S$, $NO_x$, and $SO_2$. Detection limits as low as 4 PPM can be achieved for $H_2S$ and $NO_x$ gases with polyaniline gas sensors (See, e.g., "Polyaniline Thin Films For Gas Sensing" by N. E. Agbor et al., Sensors and Actuators B28, 173–179 (1995)). In a variation of these measurements U.S. Pat. No. 5,252,292 for "Ammonia Sensor" which issued to Hirata et al. on Oct. 12, 1993 describes an ammonia sensor consisting of at least one pair of electrodes and an ammonia-sensing material comprising a polyaniline filling the space between the electrodes. Therein, the polyaniline changes its electric resistance in proportion to the ammonia concentration in an atmosphere such as air or other gas and accordingly the measurement of the electric resistance enables the detection of the ammonia concentration at a high sensitivity.

Recently, high-frequency and multi-frequency ac conductivity measurement techniques have been used for conducting polymer gas sensors (See, e.g., "High-Frequency a.c. Investigation Of Conducting Polymer Gas Sensors" by F. Musio et al., Sensors and Actuators B23, 223–226 (1995) and "Multi-Frequency Measurements Of Organic Conducting Polymers For Sensing Of Gases And Vapors" by M. E. H. Amrani et al., Sensors and Actuators B33, 137–141 (1996)).

The most important advantage of ac conductivity measurements is that it is possible to distinguish different chemical species with a single sensor. Organic vapors, such as methanol, acetone, and ethyl acetate, were detected by measuring a.c. conductivity changes of a polyaniline gas sensor at different frequencies (M. E. H. Amrani et al., supra). Another technique, which can differentiate different chemical species, is the frequency counting interrogation technique (See, e.g., "Frequency Counting Interrogation Techniques Applied To Gas Sensor Arrays" by M. E. H. Amrani et al., Sensors and Actuators B57, 75–82 (1999). In order to monitor characteristic resistance and capacitance changes simultaneously, a conducting polymer sensor was used as one of the arms of a four-channel Wien-bridge oscillator system. From the combined patterns of frequency changes in the four channels, it was possible to detect the vapor to which the system was exposed.

There are a few reports of conducting polymers being used for optical gas sensors (See, e.g., "An Optical Gas Sensor Based On Polyaniline Langmuir-Blodgett Films" by N. E. Agbor et al., Sensors and Actuators B41, 137–141 (1997)). Therein, a polyaniline optical sensor based on the surface plasmon resonance and sensitive to $NO_2$ and $H_2S$ with detection limits of approximately 50 vapor parts per million was described. However, the sensor response was slow, and total regeneration of the sensor after exposure to gases was impossible.

In U.S. Pat. No. 6,051,437 for "Optical Chemical Sensor Based On Multilayer Self-Assembled Thin Film Sensors For Aquaculture Process Control", which issued to Luo et al. on Apr. 18, 2000 describes optical chemical probes having layers of anionic and cationic polyelectrolytes and one or more dyes incorporated into these layers. The probes are placed in the medium to be analyzed and the dye or dyes react in the presence of the corresponding chemical. Color changes may be observe manually or by a photodetector. A light source may be employed to increase the optical signal received from the probe.

In U.S. Pat. No. 6,117,686 for "Method For Detecting Harmful Gases Which Is Applicable To Broad Gas Concentration Range", which issued to Tanaka et al. on Sep. 12, 2000, a method for detecting certain gases is described wherein a layer of matrix polymer which includes tetraphenylporphyrin (TPP) is used as a detector. When the concentration of tetraphenylporphyrin contained in the matrix polymer is increased, an absorption peak appears at approximately 718 nm; moreover, when the concentration of tetraphenylporphyrin is altered, the gas concentration at which the absorption peak appears also changes, as measured by transmittance or reflection of light from the detector. For example, the 718 nm feature begins to appear at a higher gas concentration when a detector containing a lower concentration of tetraphenylporphyrin is used, whereas the feature appears at a lower gas concentration when a detector containing a higher concentration of the pigment is employed. Tanaka et al. states that this phenomenon is observed specifically with tetraphenylporphyrin, and that it is possible to detect and quantify certain gases over a broader range of concentration using a plurality of detectors containing tetraphenylporphyrin in different concentrations in a matrix polymer.

Accordingly, it is an object of the present invention to provide an ammonia gas sensor based on polyaniline which is suitable for analytical chemistry use.

Another object of the invention is to provide an ammonia gas sensor based on polyaniline having rapid response time and capable of rapid regeneration.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for quantitatively determining the amount of ammonia in a fluid hereof includes: a transparent polyaniline film; means for exposing the film to a fluid containing ammonia such that ammonia is absorbed onto the polyaniline film; means for directing light having a chosen wavelength through the film; means for detecting the light passing through the film; and means for comparing the amount of light passing through the film with the amount of light detected when there is not ammonia present in the fluid, whereby the amount of ammonia in the fluid is quantitatively determined.

Benefits and advantages of the invention include a robust portable, quantitative, sensitive ammonia detector having rapid response time and rapid regeneration capability.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Briefly, the present invention includes a robust portable, sensitive, quantitative ammonia detector based on changes in the electronic absorption spectrum of a polyaniline film prepared by chemical oxidation upon exposure to ammonia gas at room temperature. The present ammonia detector has been found to be sensitive, stable, rapid in response, easy to regenerate after exposure, and effectively eliminates the limitations associated with present conducting polymer gas sensors which employ conductivity measurements.

Reference will now be made in detail to the preferred embodiments of the present invention examples of which are illustrated in the accompanying drawings.

A. Polyaniline film preparation:

Polyaniline films were prepared following the method described in "Optical Sensing Of pH Using Thin Films Of Substituted Polyanilines" by E. Pringsheim et al., Analytica Chimica Acta 357, 247–252 (1997) with a slight modification. A length of polyethylene tube (id 3.5 mm, od 4.2 mm) was filled with a 1 M hydrochloric acid solution containing 0.1 M aniline and 0.1 M ammonium persulfate. The polymerization reaction was allowed to proceed for greater than two hours at room temperature. A uniform polyaniline film was deposited on the inner wall of the polyethylene tube. The tube was then rinsed repeatedly with deionized water to remove loose polymer particles. Generated films were treated with 0.1 M hydrochloric acid before use. A Pyrex glass tube (2 mm, id; 4 mm, od) was also tested for preparation of polyaniline films, but uniform films were difficult to obtain. Treatment of the glass with 0.1 M hydrochloric acid solution was found not to improve the quality of the film.

Figure 1:
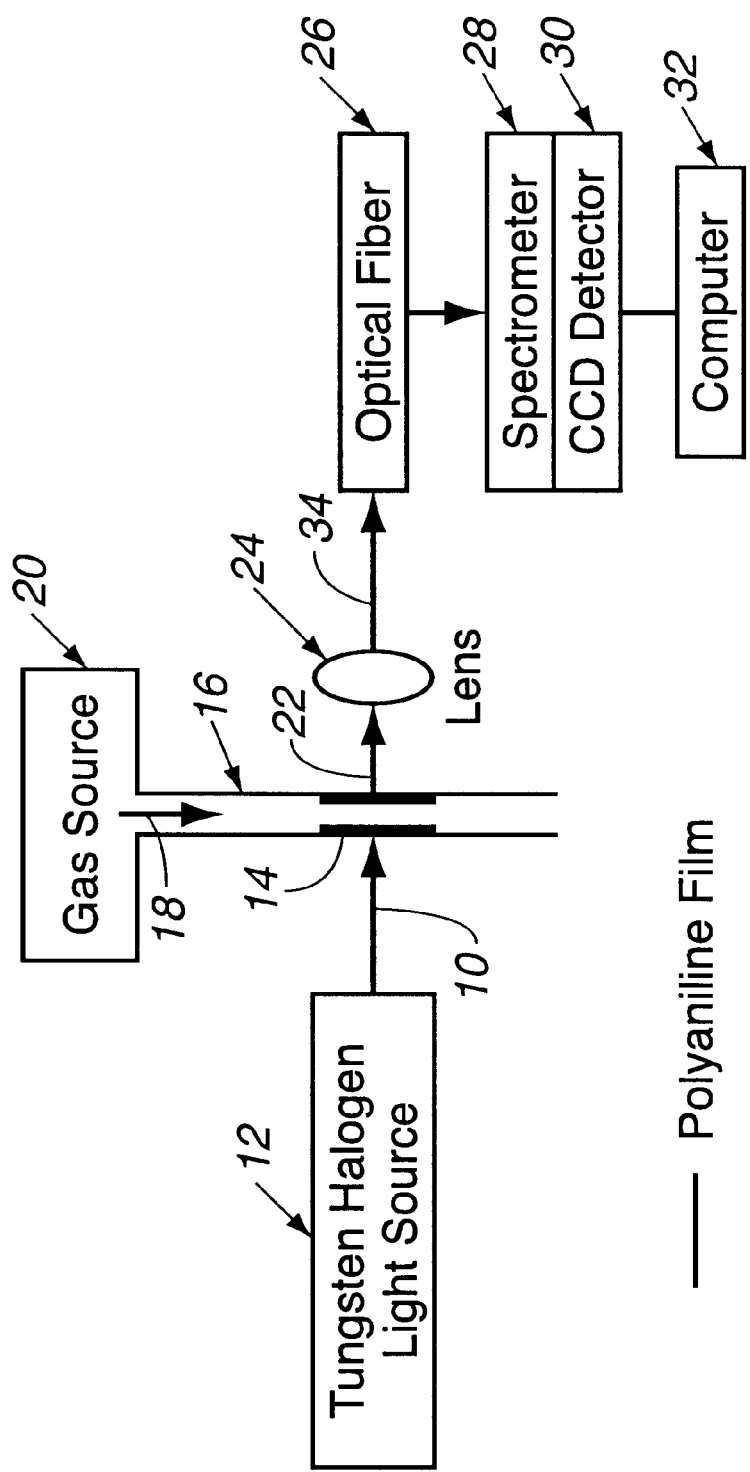
FIG. 1 is a schematic representation of the apparatus of the present invention showing the use of electronic absorption spectroscopic measurements to quantitatively detect ammonia gas.

B. Electronic absorption spectra measurements:

One embodiment of the optical ammonia gas sensing apparatus of the present invention is schematically represented in FIG. 1 hereof. A beam of light, 10, from light source, 12, is directed into a polyaniline film, 14, located inside of a transparent tube, 16, through which gas, 18, is caused to flow from gas source, 20. This can be achieved by evacuating tube 16 downstream from polyaniline film 14, or by pressurizing tube 16 upstream from polyaniline film 14. Light, 22, passing through and exiting tube 16 is collected using optical beam collection means, 24, and directed by means of an optical fiber, 26, into a commercial UV-visible spectrometer, 28, having CCD detector, 30, as a quantitative light detector, and computer, 32, for data collection and analysis. The light source employed was a tungsten halogen light source powered by a 12 VDC power supply. Optical beam collection was achieved using a collimating lens (24) to convert divergent optical beam 22 into focused beam, 34. Optical fiber 26 was a silica-core, silica-clad single-strand fiber 2 m long and 400 μm in diameter and was connected to collimating lens 24 and spectrometer 28 using SMA terminations. The spectrometer system was optimized for the wavelength range between 360 and 900 nm. The 2048-element linear CCD-array detector 30 was mounted on a 1 MHz ISA-bus A/D card and inserted in an ISA slot of a desktop computer. Stream 18 of nitrogen gas containing ammonia was passed through the polyaniline gas sensor and spectroscopic measurements were performed to determine the characteristics of the detector. Nitrogen gas (99.99%) was used as both carrier and dilution gas to transfer ammonia to the sensor. All spectroscopic experiments were performed at room temperature.

Figure 2:
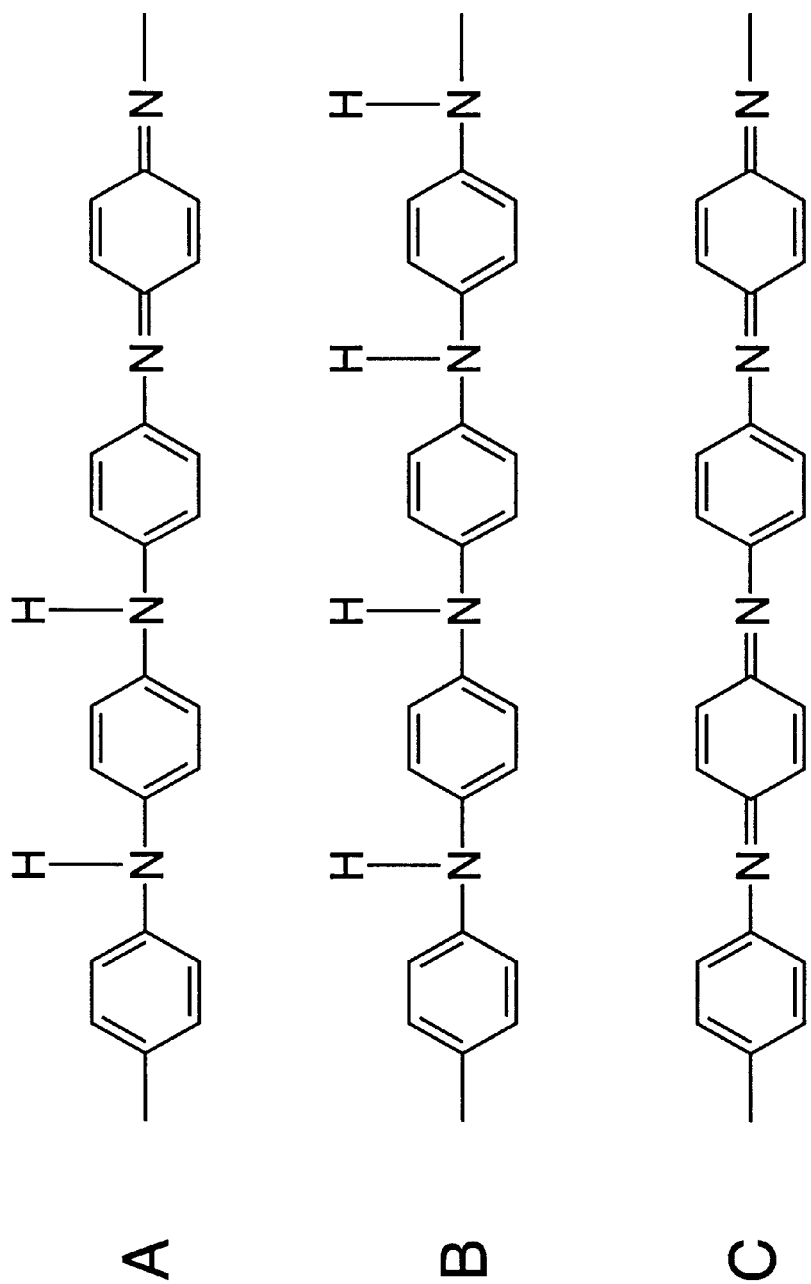
FIG. 2 illustrates the chemical structure of polyaniline for its oxidation states.

C. Ammonia gas sensing:

FIG. 2 is a schematic representation of the three oxidation states of polyaniline. The basic form of polyaniline, commonly known as emeraldine base (FIG. 2A), can be reduced to the leucoemeraldine base (FIG. 2B) or oxidized to the pernigraniline base (FIG. 2C) forms of polyaniline. When ammonia gas is adsorbed on an emeraldine base polyaniline film, it reacts with the film to generate a protonated form of polyaniline, resulting in significant changes in the electrical conductivity and electronic absorption spectrum of the film.

Figure 3:
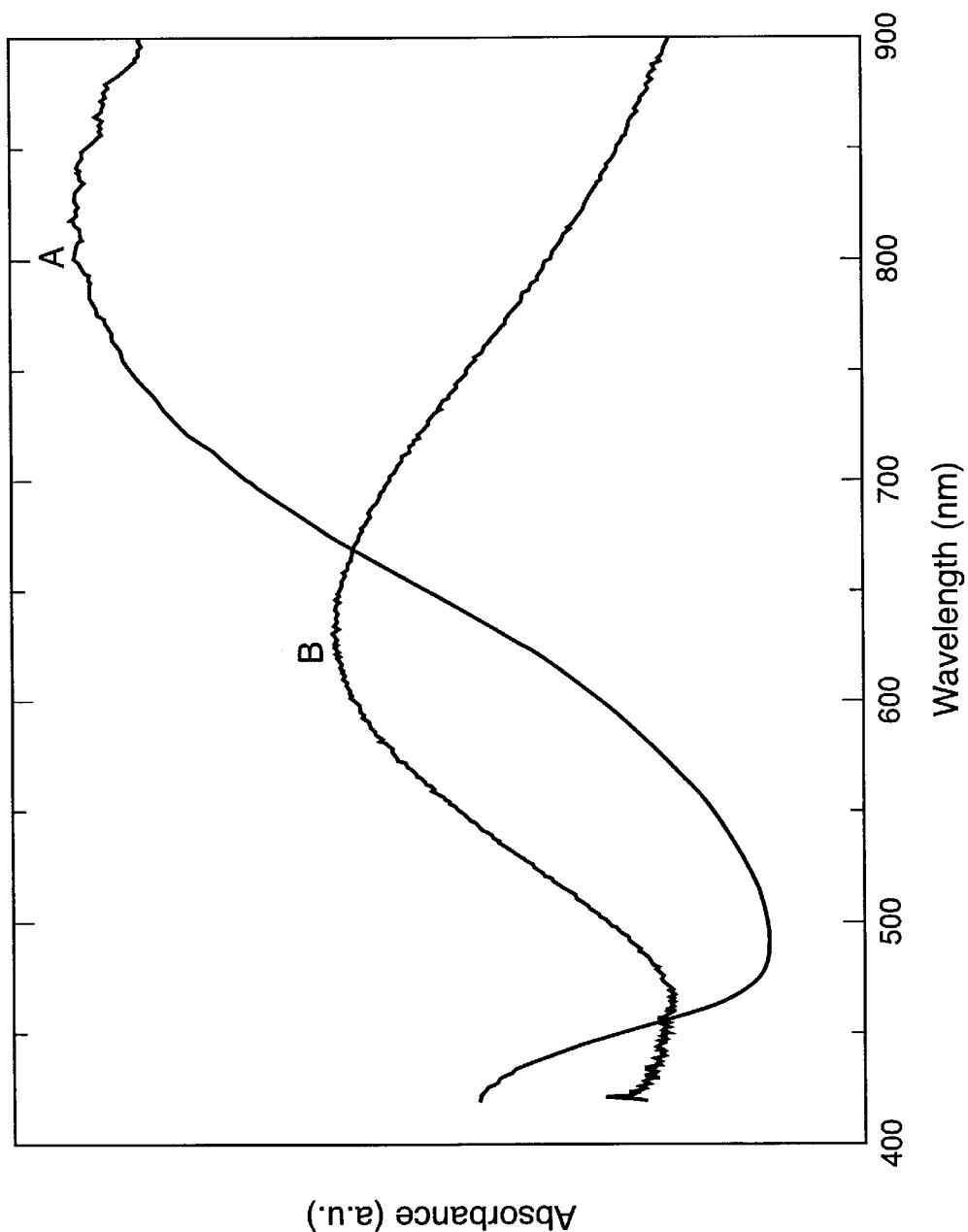
FIG. 3 shows changes in the visible spectrum for a polyaniline film as a result of protonation/deprotonation: (A) in 0.1 M hydrochloric acid; and (B) in 18,000 ppm ammonia.
Figure 4:
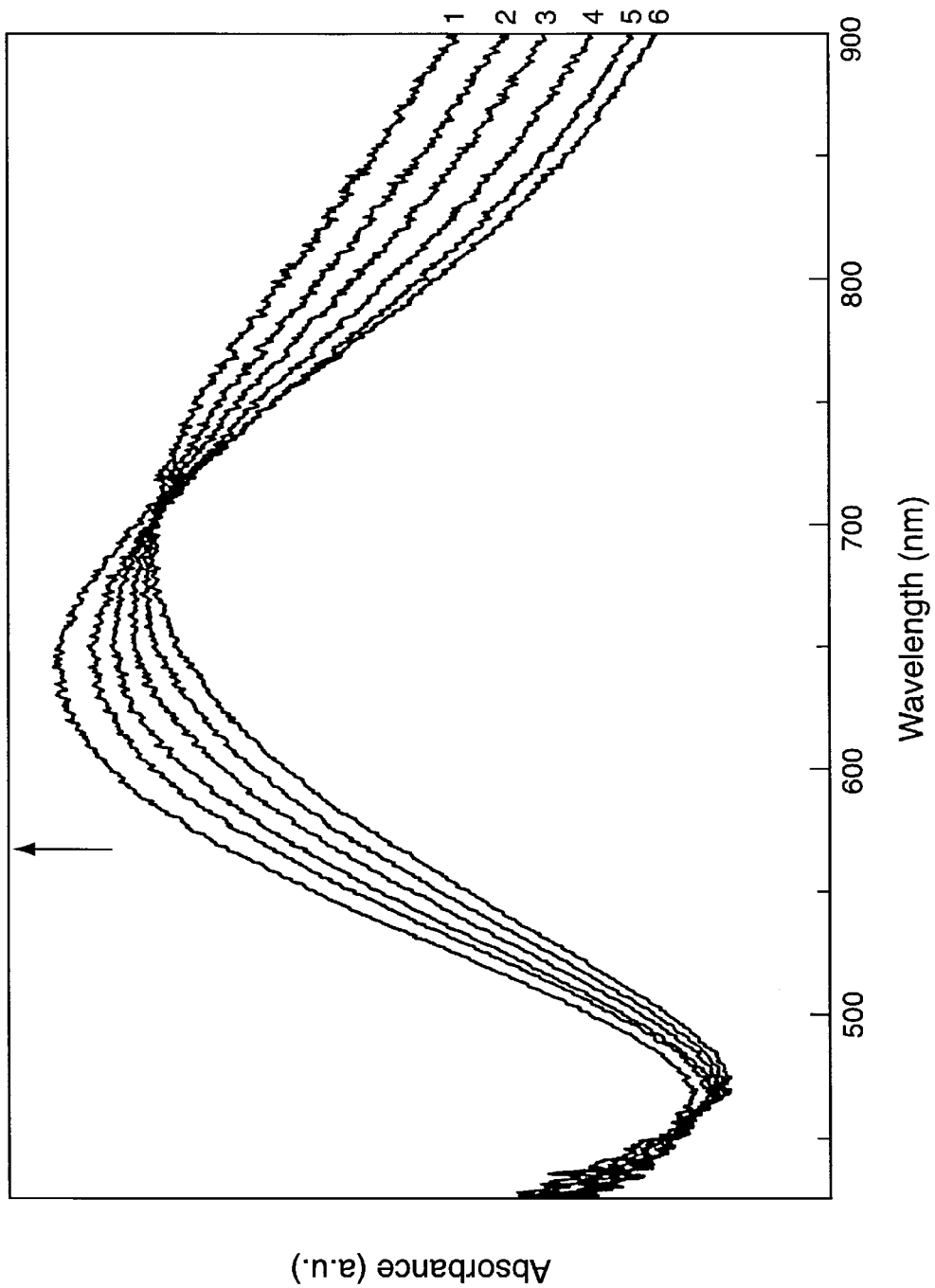
FIG. 4 shows the effect of different concentrations of ammonia gas on the spectrum for a polyaniline film for several ammonia concentrations (ppm): (1) 225; (2) 450;(3) 900; (4) 1800; (5) 9000; and (6) 18,000.

FIG. 3 shows the effect of ammonia gas on the UV-vis spectra of polyaniline films. FIG. 3A is plot of the absorbance versus wavelength for a polyaniline film treated with hydrochloric acid. A distinct green color was observed with a maximum absorbance at 800 nm confirming that the film was totally protonated. The spectrum of the film was found to be sensitive to ammonia gas. For example, when nitrogen gas containing 18,000 ppm ammonia was passed through the detector at a flow rate of 0.4 l/min, a color change from green to blue was observed as is shown in FIG. 3B, and the absorption maximum shifted to 620 nm. FIG. 4 shows the effect of different concentrations of ammonia gas on the spectra of a polyaniline film. The maximum absorption wavelength shifts gradually to shorter wavelengths with increasing ammonia concentration. In order to obtain reproducible results, spectra were measured after a one minute equilibration with the gas samples. The spectrum change is reversible, indicating that polyaniline films are useful as optical ammonia gas sensors. At 600 nm, an increase in ammonia concentration from 18 to 18000 ppm produced a four-fold increase in the absorbance. From these measurements, the detection limit for ammonia is estimated to be about 1 ppm. This sensitivity is similar to those reported for other ammonia gas sensors.

Figure 5:
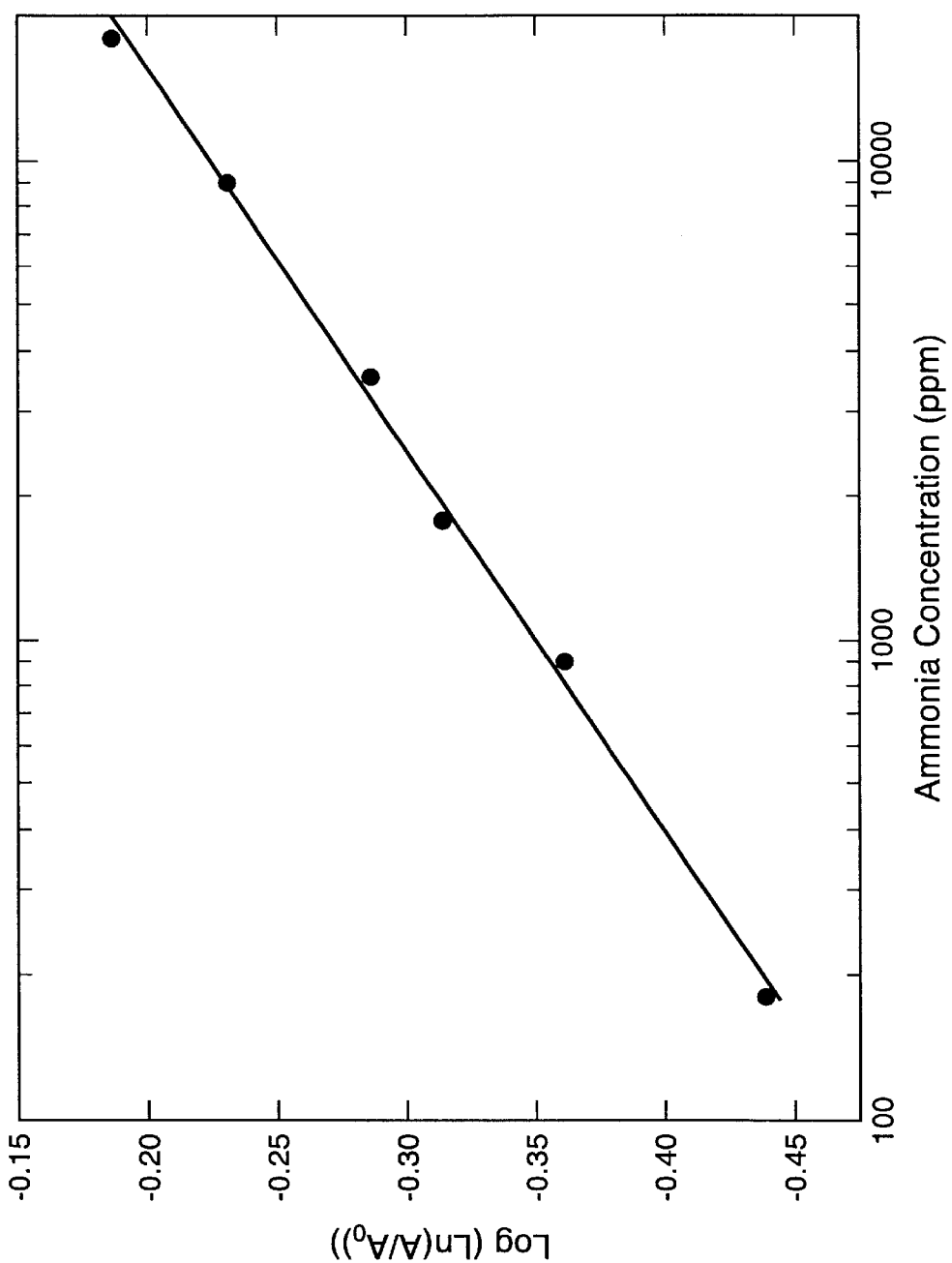
FIG. 5 is a calibration curve for the ammonia sensor of the present invention using the apparatus of FIG. 1 hereof.

The absorbance change of a polyaniline film is controlled by ammonia diffusion into the film, which can be expressed by the equation:

$$A = A_0 \, exp[(\alpha N)^\gamma]$$

where $A_0$ is the initial absorbance, A is the absorbance at concentration N, and $\alpha$ and $\gamma$ are constants. From this equation, $\log(\ln(A/A_0)$ is proportional to $\log N$. A typical calibration curve obtained using this relationship is shown in FIG. 5. The linear range is seen to be from 180 to 18000 ppm with a linear regression coefficient of 0.998. There is a slight deviation from linearity at a lower ammonia concentrations (<180 ppm) which is not shown in FIG. 5. It is believed by the present inventors that the treatment of the film with 0.1 M hydrochloric acid before each calibration may contribute to the loss of ammonia gas thereby resulting in the deviation from the straight line at lower ammonia concentrations. It should be mentioned that in accordance with the teachings of the present invention, the fluid containing ammonia includes liquids as well as gases.

Figure 6:
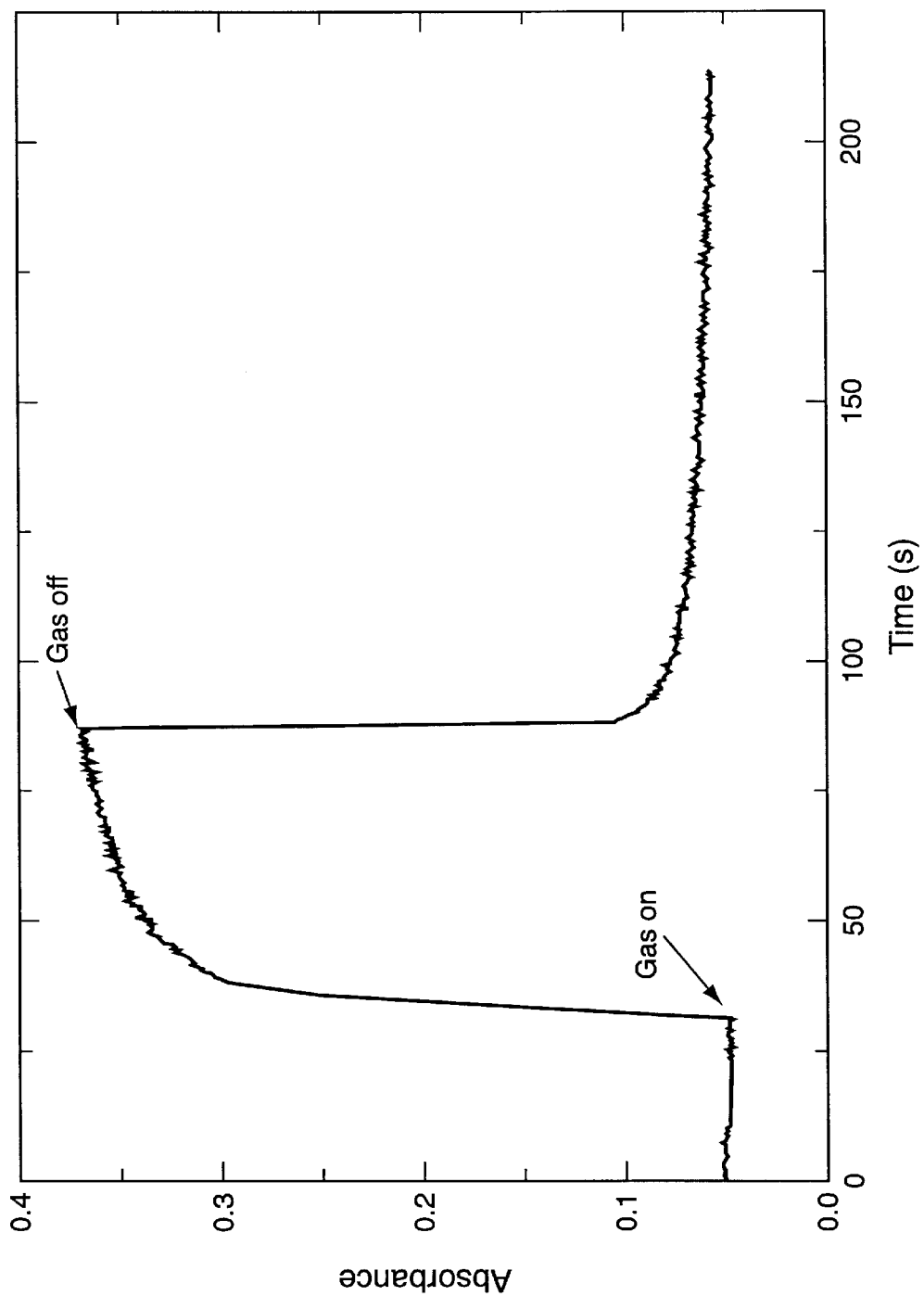
FIG. 6 shows the response of the sensor to contact with ammonia (admission-removal cycles) at 620 nm and a gas flow rate of 800 mi/min, where gas on indicates a stream of nitrogen gas containing 200 PPM ammonia passed through the sensor, while gas off indicates that a stream of pure nitrogen gas was passed through the sensor.

D. Polyaniline film response and regeneration:

FIG. 6 shows a single cycle response of a polyaniline film to ammonia uptake followed by regeneration in a nitrogen gas stream at room temperature. The absorbance at a wavelength of 620 nm for an ammonia concentration of 200 ppm is approximately 90% within 15 seconds. When the ammonia is removed from the gas stream, the absorbance decreases to less than 10% of its peak height within 10 seconds. The absorbance is observed to be 2.5% higher than the original baseline after two minutes of exposing the polyaniline film to a stream of pure nitrogen gas at room temperature. The present optical ammonia gas sensor can be fully regenerated by treating it with a dilute hydrochloric acid solution at room temperature. This treatment results in the rapid formation of a green film and a complete regeneration of the sensor. As an alternative method, a nitrogen gas containing hydrochloric acid can be used to regenerate the sensor.

By comparison, it is not possible to regenerate a polypyrrole ammonia gas sensor after exposing it to 10 ppm ammonia. Polyaniline-based ammonia gas sensors utilizing conductivity measurements have a response time of about 2 min., and can only be partly regenerated by passing air through the sensor to remove the ammonia adsorbed on the surface. In order to fully regenerate the sensor, a thermal method, whereby the sensor is heated to 104–107° C. was proposed. Hydrochloric acid regeneration is likely to adversely affect these detectors, since conductivity measurements are likely to be more affected by trace ammonia and moisture than the detector of the present invention.

Conducting polymer-based ammonia gas detectors utilizing electronic absorption spectroscopy in accordance with the present invention have been found to have significant advantages over the conventional sensors based on conductivity measurements not only in response and regeneration time, but also in ease of sensor regeneration.

The foregoing description of the invention has been presented for purposes of illustration and description and is not intended to be exhaustive or to limit the invention to the precise form disclosed, and obviously many modifications and variations are possible in light of the above teaching. For example, it would be apparent to one having skill in the art after reviewing the teachings of the present invention that light reflected from the conducting polymer film could also be used for detecting the presence of ammonia thereon. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for quantitatively determining the amount of ammonia in a fluid comprising, in combination:

(a) a transparent film consisting essentially of polyaniline;

(b) means for exposing said polyaniline film to a fluid containing ammonia such that ammonia is adsorbed onto said polyaniline film;

(c) means for directing light having a chosen wavelength through said polyaniline film;

(d) means for detecting the chosen wavelength of light passing through said polyaniline film; and (e) means for comparing the amount of light detected by said means for detecting light passing through said polyaniline film with the amount of light detected by said means for detecting light passing through said polyaniline film when there is no ammonia present in the fluid, whereby the amount of ammonia in the fluid is quantitatively determined.

2. The apparatus as described in claim 1, wherein the chosen wavelength of light is in the range between 360 and 900 nm.

3. The apparatus as described in claim 2, wherein the chosen wavelength of light is 620 nm.

4. The apparatus as described in claim 1, wherein said transparent polyaniline film is exposed to acidic or neutral gases between measurements of the quantity of ammonia in a fluid.

5. The apparatus as described in claim 4, wherein the acidic gases comprise hydrogen chloride.

6. The apparatus as described in claim 1, wherein said fluid is a gas having ammonia as a constituent.

\* \* \* \* \*